United States Patent [19]
Westcott

[11] 4,047,814
[45] Sept. 13, 1977

[54] METHOD AND APPARATUS FOR SEGREGATING PARTICULATE MATTER

[75] Inventor: Vernon C. Westcott, Lincoln, Mass.

[73] Assignee: Trans-Sonics, Incorporated, Burlington, Mass.

[21] Appl. No.: 631,171

[22] Filed: Nov. 11, 1975

Related U.S. Application Data

[63] Continuation of Ser. No. 446,547, Feb. 27, 1974, abandoned, which is a continuation of Ser. No. 176,419, Aug. 25, 1971, abandoned.

[51] Int. Cl.² .................... G01N 1/00; G01N 33/28
[52] U.S. Cl. .................................. 356/38; 209/214; 356/70; 356/72; 356/73; 356/201; 356/206
[58] Field of Search .................... 356/36, 38, 70, 72, 356/73, 173, 186, 190, 201–206; 209/127 R, 129, 212, 214, 223 R, 223 A

[56] References Cited

U.S. PATENT DOCUMENTS

| | | | |
|---|---|---|---|
| 1,522,343 | 1/1925 | Thom | 209/223 R |
| 2,068,476 | 1/1937 | Thomas | 356/38 |
| 2,091,222 | 8/1937 | Thomas | 356/70 |
| 2,105,851 | 1/1938 | Vobach et al. | 209/223 R |
| 2,898,803 | 8/1959 | Morrison | 356/38 |
| 2,913,584 | 11/1959 | Dill | 356/38 |
| 3,289,003 | 11/1966 | Jorgeson | 356/209 |
| 3,380,584 | 4/1968 | Falwyler | 209/127 R |
| 3,477,568 | 11/1969 | Madrid | 209/127 R |
| 3,526,461 | 9/1970 | Lindahl et al. | 356/38 |

Primary Examiner—Vincent P. McGraw
Attorney, Agent, or Firm—Parmelee, Johnson & Bollinger

[57] ABSTRACT

The concentrations of hyperfine particles in a fluid are monitored by flowing a predetermined quantity of the particle-containing fluid over a substrate in the presence of a force field which "collects" the particles onto the substrate. The particles may be deposited on the substrate according to size, so that one can readily ascertain not only the particle concentration in the fluid, but the size distribution of the particles as well. This technique greatly concentrates the particles so that one can usually detect and monitor materials having extremely small particulate concentrations in the fluid from which they are collected.

47 Claims, 23 Drawing Figures

METHOD AND APPARATUS FOR SEGREGATING PARTICULATE MATTER

This is a continuation, of application Ser. No. 446,547 filed Feb. 27, 1974, now abandoned which in turn is a continuation of U.S. application Ser. No. 176,419, filed Aug. 25, 1971, now abandoned.

BACKGROUND OF THE INVENTION

A. Field of the Invention

The invention relates to the detection of hyperfine particles in a fluid and the optical determination of their type and size distribution. It also relates to the analysis of wear of moving parts, such as jet engine bearings and to the testing of the performance of various lubricants.

B. Prior Art

Frequently it is necessary or desirable to monitor certain characteristics of particles in a fluid, such as particle type (e.g. pure metal, oxide, sulfide, etc.), size, and concentration among others. For example, in connection with machinery having moving parts which reciprocate or rotate with respect to one another, a lubricating oil is generally applied to the moving parts to minimize friction between the parts and attendant wear. In many cases, lubrication does not completely eliminate all wear, however, and material is continuously abraded from the machinery during use. The lubricating oil carries away these abraded particles. Examination of the particles suspended in the oil enables one to monitor operation of the machinery and thereby detect incipient failures. Frequently, the particles are of extremely small size (e.g. having maximum dimensions from a few microns down to a hundredths of microns; these are hereinafter termed "hyperfine").

The concentrations of small amounts of various substances in a fluid are frequently measured by chemical or spectrometric techniques. Both of these are primarily laboratory-type techniques in that they often require expensive and complex equipment which is not readily adapted for in situ measurements. Additionally, these techniques are inadequate for determining characteristics of particles in a fluid, such as particle size distribution, or the rate at which this distribution changes, which I have found to be of great assistance in predicting machinery failures from wearing parts.

Liquid suspensions are also commonly examined with the aid of a microscope to determine characteristics of the particles suspended in them. This is done by transmitting light through the liquid and observing the light reflected or refracted into the microscope by the particles. However, this technique is inadequate for examination of suspensions of hyperfine particles of low concentration (e.g. several parts per million) since they are too small to significantly disturb the wavefront of the light incident on them. Further, even somewhat larger particles are not photographed in suspension without difficulty since their Brownian motion "blurs" the observation, expecially over an extended time period.

BRIEF SUMMARY OF THE INVENTION

A. Objects of the Invention

Accordingly, it is an object of the invention to provide improved method and apparatus for monitoring foreign substances carried in minute concentrations and in particulate form.

Further, it is an object of the invention to provide improved method and apparatus for analyzing a fluid to determine the concentration of hyperfine magnetic particles therein.

Yet another object of the invention is to provide improved method and apparatus for determining the wear characteristics of machinery.

Another object of the invention is to provide improved method and apparatus for predicting machinery failure characterized by wearing parts.

A still further object of the invention is to provide method and apparatus for analyzing the concentration of iron particles in machinery fluids in situ in normal operation.

A further object of the invention is to provide improved method and apparatus for testing the performance of lubricating oil.

B. Brief Description of the Invention

In accordance with my invention, I analyze hyperfine particulate substances in a fluid by collecting the particles and classifying them in particulate form. I have found that in certain cases more accurate conclusions can be drawn from a number of attributes of the particles themselves, as opposed to information based on aggregate characteristics of the type resulting from spectrographic or chemical analysis. Indeed, by concentrating the particles on a substrate as described below, I am actually able to examine them visually with the aid of a microscope and thereby readily ascertain such characteristics as particle size and size distribution, particle shape and, to some extent, even the chemical makeup of individual particles. Such information is, of course, lost when the particles are destroyed in the course of the chemical and spectrographic analyses used prior to the present invention. Yet, I have found it to be most important in analyzing the wear characteristics of moving parts or, conversely, the deposits in lubricants for those parts.

To concentrate the suspended particles I flow a particle-containing fluid over a collecting substrate in the presence of a magnetic or electric field having an intense gradient. The field causes magnetically susceptible or electrically polarizable particles, as the case may be, to settle on the substrate at a rate which is proportional to their concentration in the fluid, as well as to the flow rate of the fluid over the substrate. Thus, by examining the deposited material after a fixed time interval, their concentrations can be monitored. Repeated examinations disclose the manner in which the concentration changes with time.

The particles are deposited on the substrate in accordance with their size, the larger particles being deposited first and the smaller particles being deposited last. This arises from the fact that the field forces pulling a particle onto the substrate are a function of the volume of the particle, while the viscous retarding forces are a function of its surface area. Thus, larger particles, having a greater ratio of volume to surface area, are pulled from the fluid first. The result is a stripe of deposited material on the substrate, with particle size varying gradually from one end of the stripe to the other. The stripe will generally be visible to the naked eye and one can therefore obtain a rough idea of particle size distribution merely by a cursory observation of the relative darkness of various portions of the stripe. For accuracy, however, more refined procedures should be used as described below.

In one embodiment of the invention used in analyzing the magnetic particle content of a liquid, I position a thin flat glass slide several inches long across the gap of a strong magnet so as to provide a highly divergent magnetic field at the top surface of the slide having gradient components of the order of several hundred kilogauss/inch. Iron or other magnetic particles suspended in the liquid are deposited on the substrate under the force of the magnetic gradient.

In the preferred embodiment, the slide is positioned with its long dimension parallel to the gap between the pole pieces and with one end slightly elevated above this gap (for example by about 1°). This establishes a gradually increasing field intensity along the flow path of the fluid so that particles in the fluid are deposited along the length of the substrate in accordance with their size; this provides a more informative indication of the wear characteristics of a machine from which the fluid sample is taken. Specifically, the larger particles precipitate first while the smaller particles precipitate last, thus establishing a size distribution from large to small along the flow path.

After a sufficient quantity of fluid has flowed down the substrate, the substrate is then dried and optically examined to determine particle concentration. Optical examination of hyperfine particles is enabled by virtue of the fact that the particles are greatly concentrated on the substrate by my collection process. The examination may be accomplished by visual methods, such as with the aid of a microscope, or it may be accomplished photometrically, for example, by means of a densitometer which may be used to scan the substrate and which provides an output proportional to the density of particles in a given area. In addition, since the particles are greatly concentrated by my technique, conventional chemical and spectrographic tests can be made on them more easily.

When the examination is to be by microscope, the liquid is first evaporated from the slide to minimize undesired interference effects. The examination is preferably conducted with a microscope having a high numerical aperture (e.g. 0.65 or greater) and which operates with both reflected and transmitted light. Such microscopes are commercially available. Additionally, however, I color the illuminating lights to achieve unique results. For example, I have found that inserting color filters of different colors in the light paths (e.g. a red filter in the incident light path and a green filter in the transmitted light path) enables one to observe characteristics of the precipitate which are not otherwise readily observable. For example, one can distinguish metals (which block the green transmitted light and reflect the red incident light and thus appear reddish) from their oxides or sulfides (which pass the green transmitted light and thus appear as a combination of the two colors, i.e. yellowish), even when the particles being examined are less than a micron in size.

When a viscous fluid such as engine oil is being examined, the collection of the particles onto the substrate under the influence of the magnetic field may be promoted by adding a solvent "developer" to the oil. The developer loosens the bonds between the particulate material and the oil (or additives in the oil) and thus promotes faster particle precipitation. After the appropriate amount of fluid has been flowed over the substrate, the latter is then preferably washed with a solvent which removes the remaining liquid from the surface of the substrate and leaves the particles attached to this surface, thus serving as a "fixer." The substrate is then examined as described above.

The preceding embodiment of the invention is primarily suited for measurements of particle characteristics apart from the fluid source. A second embodiment, which is more especially adapted for in situ measurements, such as within the oil chamber of an engine, has a translucent tube, e.g. of glass, through which the fluid to be analyzed is flowed. The tube is mounted within a housing which may be inserted directly into a line through which the fluid passes. The housing also incorporates a magnet having pole faces extending parallel to each other and along the length of the tube to establish a diverging magnetic field at the interior surface of the tube. As before, the tube is slightly inclined to the plane of the gap between the pole pieces to establish a gradually increasing field as the flow path is traversed so as help segregate particles according to size.

A light source and densitometer are also mounted within the housing and on opposite sides of the tube. The fluid to be analyzed, such as engine oil, is flowed through the tube at a known flow rate and the particle quantity collected after a predetermined time is measured by means of the densitometer. The output of the densitometer is a direct function of particle concentration in the fluid. This concentration may be displayed directly for the information of the operator; alternatively, it may be applied to a processor which operates on the data before display. For example, the processor may compute the ratio of the concentration of particles at a given position on the tube at two or more different intervals of time. It may also calculate other quantities, such as the ratio of particle density at two different positions on the tube at a given time, and may further determine the rates at which this ratio changes.

As noted previously, the particles in the fluid are collected along the substrate in accordance with their size. By examining not only the concentration of particles of a particular size but also the relative concentrations of different sizes and the rates at which the concentrations and relative concentrations change from sample to sample in a fluid such as machinery lubricant, much information can be gleaned regarding the operating performance of machinery. Specifically, I have found that incipient failures can actually be predicted. More particularly, during normal wear, small particles will be continually eroded from machine surfaces at rates which are dependent on the particular machine. A lesser number of larger particles will also normally be eroded. Under normal conditions, the rates or erosion of the small particles and the large particles will bear a relatively constant relation to each other. However, with the onset of abnormal wear, the rate of erosion of the large particles relative to the small particles suddenly increases (due, I believe, to metal to metal contact) and this signals incipient failure.

With the method of the present invention, I have been able to predict engine failure from engine oil samples taken long before failure occurred. Indeed, I have been able to detect a telltale buildup of particles pointing toward engine failure long before conventional spectrometric analysis revealed any undue buildup in concentration.

By the same token, using my technique, one can test or check the performance of various lubricants, such as engine oil. In this procedure, standard contacting machine parts, e.g. two meshing gears, are operated in the lubricant being tested. Then engine oil samples are taken periodically. The time which elapses before a buildup of large particles eroded from the gears thus provides an indication of the efficacy of the lubricant. It is important to appreciate at this point that with my technique, the performance results can be obtained in a matter of minutes, instead of the hours required using conventional methods.

The detection of electrically polarizable particles is achieved in an analogous manner, that is, a non-uniform electric field intersecting the flow path of the particle-containing fluid is established and the particles thus collected on a substrate by means of the field are examined. As before, the particle concentration, sizes, size distributions, and time rate of change of these distributions are of great interest. Because of the great importance of iron in moving machinery, especially engines, however, the following discussion will concentrate on this aspect of the invention, although it will be understood that it is not so limited. Further, it should also be understood that the term "iron" as used herein is meant to include all magnetic forms of iron, such as steel and other iron alloys, as well as magnetic compounds of iron.

DETAILED DESCRIPTION OF THE INVENTION

The foregoing and other and further objects and features of the invention will be more readily understood on reference to the following detailed description of the invention in conjunction with the accompanying drawings in which.

Figure 1:
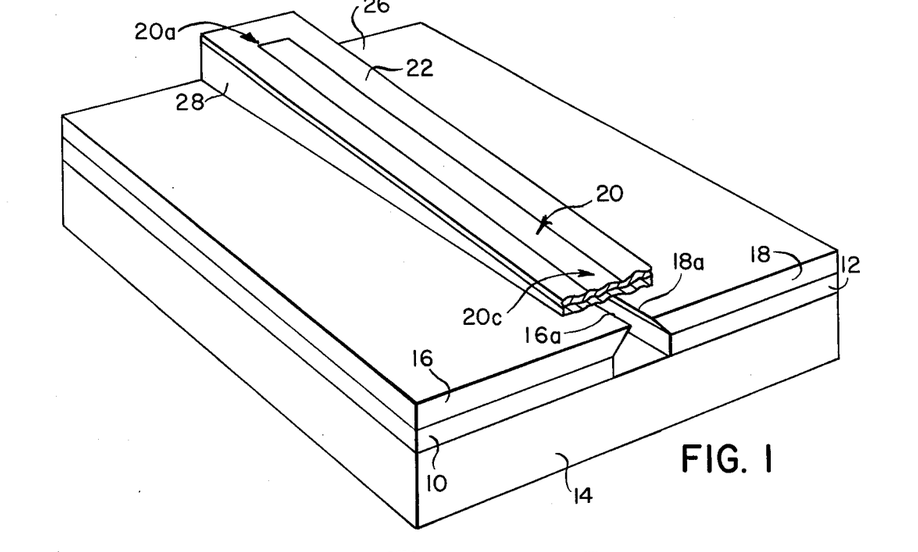
FIG. 1 is a pictorial view of one embodiment of apparatus for practicing the invention.

In FIG. 1, a pair of magnets 10, 12 are positioned on a magnetic return 14 and have pole pieces 16, 18, respectively, associated with them. The pole pieces have leading edges 16a, 18a, respectively, which are separated by a narrow gap so as to produce an intense field having a very high gradient in the air gap between them. This gradient is in a plane transverse to the pole piece edges and has a downwardly directed component which collects particles on a substrate 20 positioned above the magnet. In one realization of the invention in accordance with FIG. 1, I have used pole pieces of iron, 0.25 inch thick, having tapered leading edges separated by an air gap of 0.040 inch, and have projected a flux of approximately 18,000 gauss (the saturation magnetization of iron) into this air gap to achieve a strong vertical component of the flux gradient of the order of hundreds of kilogauss/inch.

Figure 7:
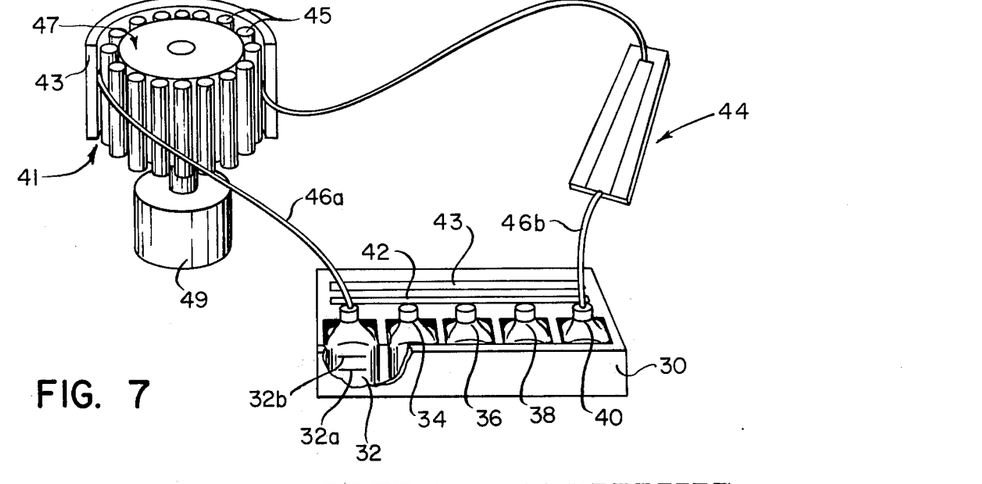
FIG. 7 is a sketch of apparatus adapted to facilitate the sampling process.

A fluid 22 containing particles whose concentration is to be monitored is flowed over the substrate at a fixed rate. The fluid is supplied to a receiving end 20a of the substrate and drained from a discharge end 20c. Apparatus especially adapted to this end is shown in FIG. 7 and described below. The substrate 20 is centered over the air gap between the pole pieces 16, 18 and is inclined at a slight angle (of the order of 1°) to the plane of the edges 16a, 18a of the pole pieces by means of a wedge 28, for example, which elevates the fluid-receiving end 20a of the substrate above the discharge end 20c. This causes the magnetic field to increase along the substrate in the longitudinal direction, since the end 20a is positioned farther from the pole pieces than the end 20c. Thus, as the fluid 22 travels down the substrate, the magnetically susceptible particles in it are subjected to an increasingly intense magnetic field gradient. This assists in segregating the particles in the fluid according to size as will be more fully described below.

Figure 2:
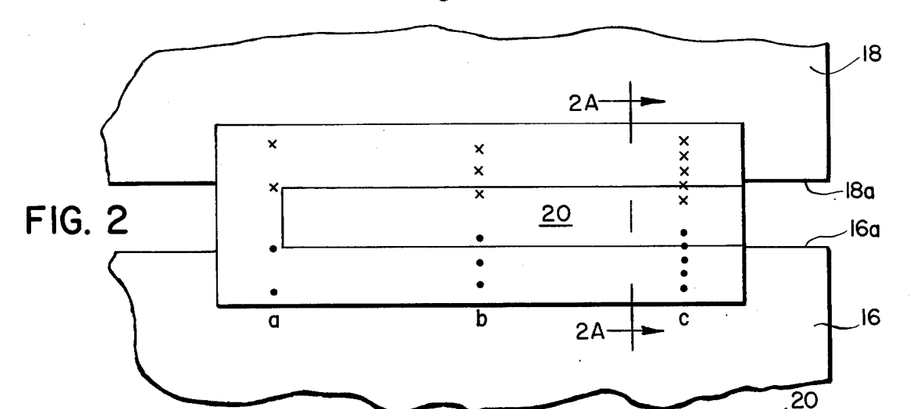
FIG. 2 is a top planar view of a portion of FIG. 1 showing the collecting substrate in more detail.

FIG. 2 is a top planar view of the substrate 20 of FIG. 1 showing, in part, the distribution of the magnetic field over the plane of the substrate. The intersection of the magnetic fields established between the pole pieces 16, 18 with the plane of the substrate 20 is illustrated by means of conventional dots and crosses, the dots representing a magnetic field vector extending outwardly from the plane of the paper and the crosses indicating magnetic field vectors extending downwardly into the plane of the paper. For the configuration shown, the field extends from the magnet 16 to the magnet 18.

As noted above, fluid traveling down the substrate (from left to right in FIG. 2) is subjected to an increasingly intense magnetic field. The larger particles have a larger ratio of volume to surface area than the smaller particles; consequently, viscous drag, which is proportional to surface area, is of lesser magnitude per unit volume for the large particles than for the smaller particles. At the same time, magnetization of the particles is roughly proportional to particle size and thus the larger particles precipitate out first, even though they are subjected to a lesser field and gradient. In consequence, the particles are distributed along the length of the substrate in accordance with their size, the larger particles precipitating out primarily at the "feed" end 20a of the slide, the smaller particles precipitating out primarily at the "exit" end 20c. Intermediate sized particles are deposited in between. Thus, the present invention provides a ready means for determining not only the rate of deposit of the particles, but also their size distribution in the fluid.

Figures 2A, 8:
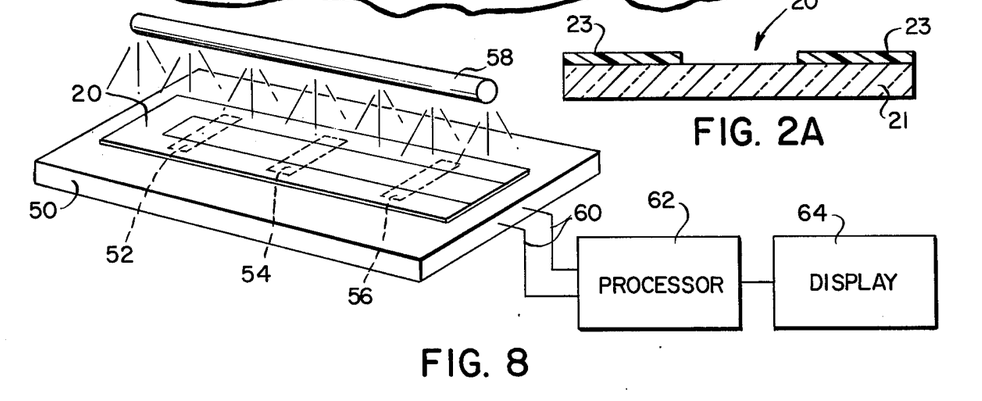
FIG. 2A is a vertical cross section through the substrate of FIG. 2.
FIG. 8 is a sketch of one form of apparatus for monitoring the build up of particles on the collecting substrate.

A cross-section of the substrate is shown in FIG. 2A. The substrate is typically formed from a thin translucent base 21 (e.g. of glass) of the order of 0.003 inch thick, 1 inch wide, and 2 inches long. Strips 23 of non-wettable material such as Teflon™ are secured to the edges of the base to form a flow-defining channel on the surface of the base.

In flowing over the substrate, the fluid being analyzed is characterized by a velocity which ranges from zero at the substrate surface to a maximum at the uppermost surface of the fluid. As particles are drawn down toward the substrate, they penetrate flow layers of successively decreasing velocity and thus their longitudinal velocity along the slide decreases. At the same time, they continue to be accelerated in the vertical direction by the magnetic forces. Accordingly, their trajectory becomes more and more steep until ultimately they impact on the substrate surface at a nearly vertical angle. The larger particles are drawn to the substrate first because of their larger volume-to-area ratio and thus are deposited at the upper or "inlet" end of the substrate. The smaller particles, characterized as they are by a smaller volume-to-area ratio, are deposited further down the slide. Of course, because of the low velocity of the fluid layers nearest the substrate surface these layers are depleted of particles, including smaller particles, first. It is thus the outermost layers which carry the majority of the smaller particles furthest down the slide. Indeed, I have estimated that approximately 50% of the particles deposited on the slide come from the outermost 20% of the fluid layer.

I have found that much valuable information concerning the condition of an engine can be obtained by monitoring not merely the particle concentration but also the particle size distribution over a period of time. Many engines in good operating condition appear to be characterized by a generally gradual increase in particle concentration in the engine oil over a period of time, with all sizes of particles partaking in the increase. The rate at which the concentration of the particles increase may differ for differing particle sizes. Typically, the concentration of the smaller particles increases at a faster rate than that of the larger particles. A sudden change in these concentrations provides a direct indication of possible engine malfunction. Thus, the particle concentration, the rate of change of particle concentration, the ratio of the concentration of particles of one size relative to another, and the ratio of the rate of change of the concentration of particles of one size relative to another, all provide sensitive "indices" by which the operating condition of the engine can be judged.

This can be seen quite dramatically in FIGS. 3-6 which are photomicrographs of engine oil samples from a military turbojet engine after the engine had operated for 5, 10 and 20 and 25 hours, respectively; the concentration of iron in the respective oil samples was determined by conventional spectrometric methods to be 2, 2, 3, and 200+ parts per million, respectively. The samples were taken on substrates 1 inch wide by 3 inches long and 0.003 inch thick. Photographs A, B and C of these figures show the concentration of large, intermediate and small particles in the oil as observed at the respective stations a, b and c shown in FIG. 2. In obtaining these samples, an oil sample of 3.5 c.c. was mixed with 1.5 c.c. of "developer" and flowed over the substrate at a rate of 10 c.c. per hour for 30 minutes. The substrate was then flushed with developer to remove all the residual oil and next flushed with "fixer" to remove the developer and fix the particles to the slide. The function of the "developer" and the "fixer" will be described more fully below.

Figure 3A:
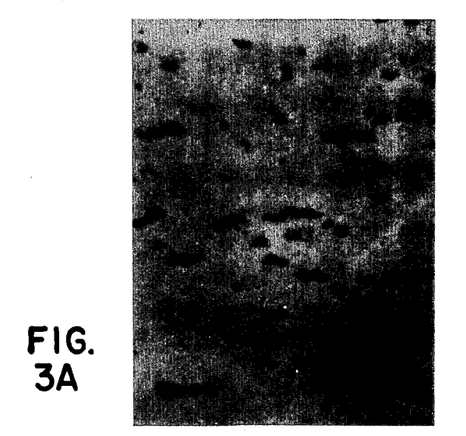
FIGS. 3A, 3B and 3C are reproductions of photomicrographs showing particle concentration at stations $a$, $b$ and $c$ of FIG. 2 in a sample of engine oil which has run for 5 hours on the engine.
Figure 3B:
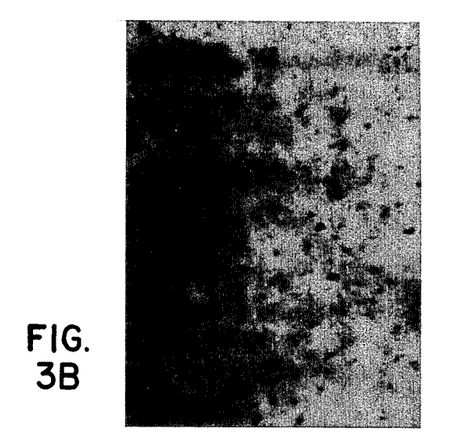
Figure 3C:
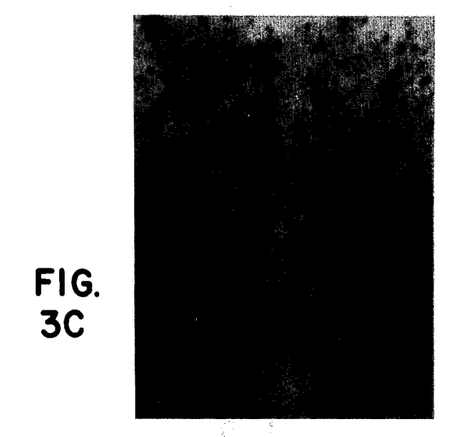

FIG. 3A shows an initial accumulation of larger iron particles which have formed themselves into short "strings" under the influence of the magnetic field. These particles are of relatively small size (approximately 1 micron) but are substantially larger than the particles in the intermediate position, FIG. 3B, or the end position, FIG. 3C. The formation of these strings after such a brief operating time on the oil (5 hours) indicates that the engine bears watching, since a number of other similar engines operating under similar conditions and free from malfunction indicates that this concentration may be excessive.

Figure 4A:
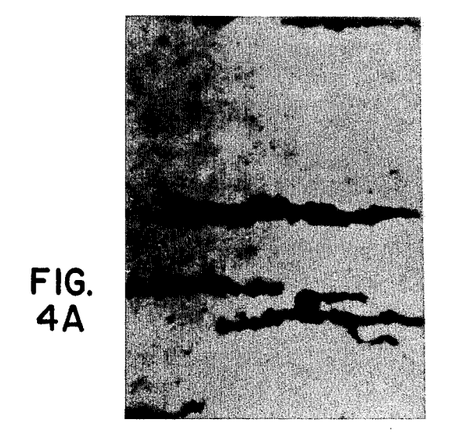
FIGS. 4A, 4B and 4C are reproductions of photomicrographs showing particle concentration in the same engine oil after the oil has run for 10 hours on the engine.
Figure 4B:
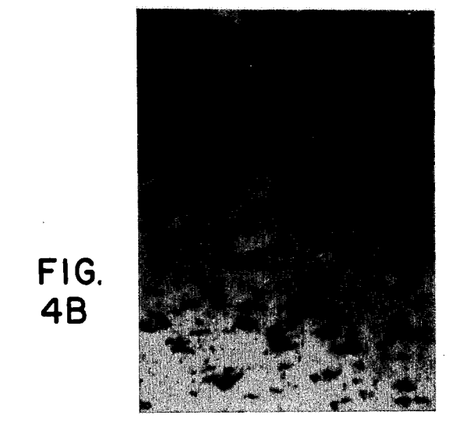
Figure 4C:
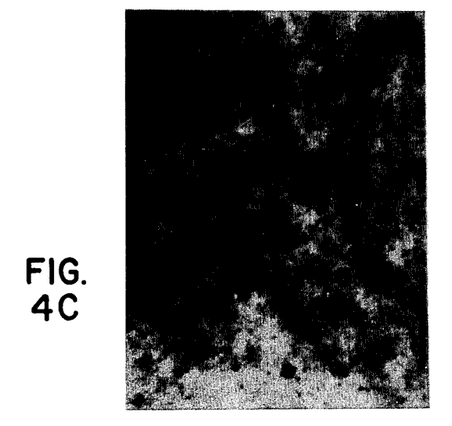

After 10 hours operating time, the oil appeared as in FIG. 4. The formation of strings in position a is much more noticeable, as is the increased concentration in positions b and c. The presence of a bent string in the lower right indicates the presence of shavings caused by metal to metal contact. At this point, the sample indicates that the engine is probably failing and an alert is justified. Note that spectrometric analysis of the oil at this time shows an iron concentration of only two parts per million and thus provides no hint of malfunction.

Figure 5A:
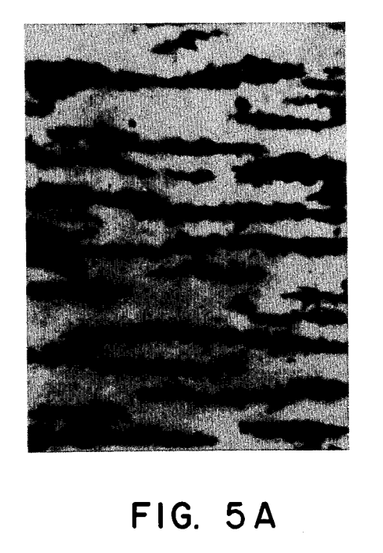
FIGS. 5A, 5B and 5C are reproductions of photomicrographs showing particle concentration in the oil after 20 hours on the engine.
Figure 5B:
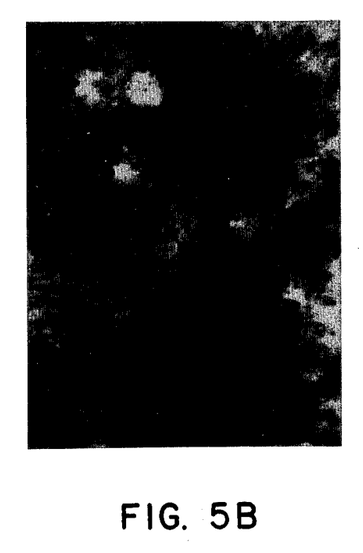
Figure 5C:
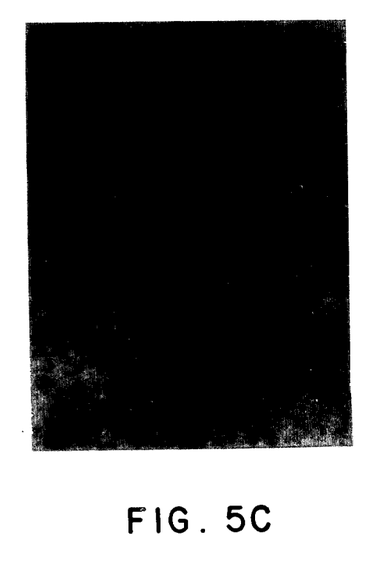

FIG. 5 shows conditions after the oil has been operated on for 20 hours. The rapid growth of the large particle strings since the last sample is quite evident. The density of the intermediate and smaller sized particles also seem to have substantially increased. This confirms the earlier prediction that excessive wear in the engine is present. Note that, as yet, conventional spectrometric techniques place the particle concentration at only three parts per million, and thus provide no warning of imminent failure.

Figure 6A:
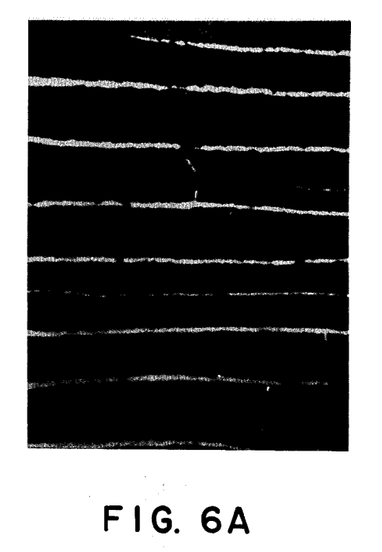
FIGS. 6A, 6B and 6C are reproductions of photomicrographs showing particle concentration after 25 hours.
Figure 6B:
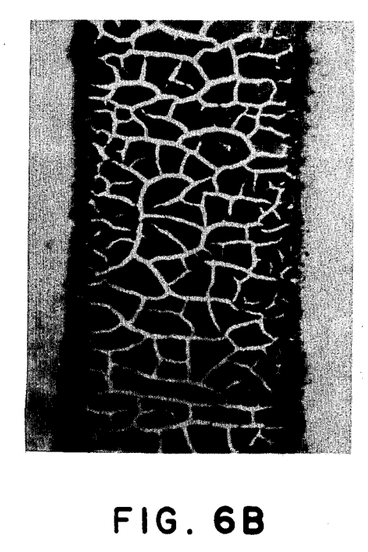
Figure 6C:
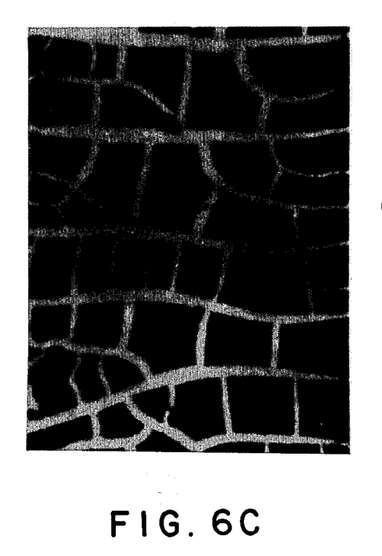

Turning now to FIG. 6, after the oil has been running on the engine for 25 hours there is a dense, opaque deposit at each station, covering almost the entire sample area: a catastrophic failure is occurring. (The white boundary lines are cracks which developed during drying of the precipitate.) At this point, the spectrometric analysis suddenly jumped to over 200 parts per million, for the first time providing a warning that the engine is failing, long after the present technique detected the incipient failure. Thus, a trend which first began to be discernible from observations in accordance with the present invention many hours prior to failure was not discernible by conventional spectrometric techniques until the failure had substantially progressed.

The time required to prepare a slide suitable for examination varies with such factors as the viscosity of the fluid to be analyzed, the particle concentration in the fluid, the intensity of the magnetic field and its gradient, and the sensitivity of the viewing apparatus, among other factors. Further, in a fluid such an engine oil, various additives are often mixed with the oil to cause the oil to stick to metal. These additives generally adhere to the metal particles and cause the oil in the immediate vicinity to gel around the particles, thereby maintaining the particles in solution longer than would otherwise be the case. To decrease the time required to obtain an appropriate sample, therefore, I find it advantageous to add a "developer" which frees the particles from the oil globules, thereby reducing particle drag and accelerating precipitation. In the case of engine oil, I have found that perchlorethylene makes an excellent "developer." It also assists by reducing viscosity.

The amount of developer to be added depends on the nature of the fluid in which the particles are immersed. For example, for oil of the type used in lubricating military-type jet engines, I add approximately 1.5 cc of developer to 3.5 cc of oil and flow the solution down the substrate at a rate of approximately 10 cc per hour for approximately 30 minutes. At the end of this time, I remove all traces of oil from the slide by flushing the slide with developer. I then remove the developer by flushing the slide with a "fixer" such as trichlorethylene. The substrate is then allowed to dry thoroughly, after which it will be found that the particles rigidly adhere to the substrate; I believe that this is due to Van der Waals' forces between the particles and the substrate due to the small particle size. In consequence, the slides may be stored for months with no measurable change in the characteristics of the particles collected on them. This procedure can reduce the time required to obtain a meaningful sample by as much as a factor of 10 from the time otherwise required.

In analyzing a fluid sample, it is necessary to guard against contamination of the sample from foreign sources. Thus, it is highly desirable to follow a systematic procedure in preparing the substrate. FIG. 7 shows a kit which is especially adapted for such a purpose.

The kit uses a container 30 having a number of bottles 32-40 used in preparing a sample. Bottle 32 is a "sample" bottle in which the fluid to be analyzed is mixed with the appropriate "developer." For this purpose, the sample bottle has a first index line 32a which marks the level to which the bottle is to be filled with the fluid to be analyzed and a second index line 32b which marks the level to which the bottle is thereafter to be filled with "developer" (if such is used). For example, with jet engine lubricating oil, the index lines may be set at 3.5 c.c. and 5.0 c.c., respectively. This facilitates mixing in the correct proportions. Bottle 34 contains a developer (such as perchlorethylene) while bottle 38 contains a "fixer" such as trichlorethylene. Bottles 36 and 40 are initially empty.

The container 30 also has a recess 42 for carrying a substrate 44 (shown removed from the container) and a recess 39 for carrying a supply of flexible tubing 46 (also shown removed from the container). The tubing is divided into two segments; a first segment 46a, which carries fluid from sample bottle 32 through a pump 41 to the upper end of the substrate, and a second segment 46b which carries spent fluid from the substrate to the receiving bottle 40. The pump 41 is of the positive displacement type and pumps fluid to the substrate by squeezing the tubing against a shell 43 by means of rollers 45; these are mounted on a cradle 47 which is rotated by a motor 49. The pump 41 does not form part of the kit but is shown to illustrate the invention more clearly.

The kit is used as follows: Substrate 44 is removed from container 30 and positioned in a diverging magnetic field, as in FIG. 1 (the source of this field is not shown in FIG. 7). The fluid sample whose particle content is to be monitored is then poured into the sample bottle up to the level of line 32a. Developer from bottle 34 is then poured into the sample bottle to fill it to line 32b. Additional developer is poured into empty bottle 36, taking care to leave some developer in bottle 34. Tubing segment 46a is then fitted to the pump 41, one end of the tubing being immersed in bottle 32, the other end being disposed at the upper end of substrate 44. Tubing segment 46b is next disposed to carry the spent fluid from substrate 44 to the discharge bottle 40.

The pump 41 is then activated to pump the fluid from the bottle 32 to the substrate 44. When the entire sample has been pumped down the slide, tubing segment 46a is removed from bottle 32 and the end that was in bottle 32 is washed in the developer in bottle 34 to remove all traces of oil from it. It is next immersed in bottle 36 and the developer in this bottle is pumped over substrate 44 to remove all traces of oil from the substrate. The end of segment 46a is then immersed in bottle 38 and the fixer in this bottle is pumped over the substrate to remove all traces of developer. Finally, the substrate is allowed to dry thoroughly and then optically examined.

The examination of the particle concentration and size distribution may be automated by means of a densitometer or similar apparatus. This is illustrated in FIG. 8 which shows a densitometer 50 having viewing stations 52, 54, 56 in the form of rectangular slits through which light can fall onto photodetectors (not shown) positioned behind the slits to measure the intensity of the light incident on them. The substrate 20 to be analyzed is positioned above the densitometer 50 and is illuminated by light from a light source 58. The amount of light from the source 58 which passes through the substrate 20 onto the slits 52-56 is a function of the diffuse optical density of the particulate deposit on the substrate which is defined as the logarithm of the ratio of the light transmitted through the substrate to light transmitted through air. The outputs of the photodetectors in the densitometer 50 are thus measures of the particle density on the substrate and they may be applied over output leads 60 to a processor 62 which facilitates determination of certain statistics of the distribution. The output of the processor is then displayed on a suitable display 64.

The processor 62 may assume any of a variety of different configurations dependent on the information which it is desired to extract from the densitometer 50. For example, it may calculate the rate at which material is being deposited on the substrate by measuring the outputs of the photodetectors in the densitometers at different times and dividing the density changes by the length of the time interval. This is the first time derivative or "rate" of material deposition. The second time derivative, or the rate at which this rate is changing, may also be of interest and the processor 62 can be adapted to determine this as well. Further, information concerning the ratios of the quantities of material deposited at one station with respect to the quantity deposited at another station is also of interest, as well as the rate at which these ratios are changing. The processor 62 may display any or all of these simultaneously or in sequence as desired.

Figure 9:
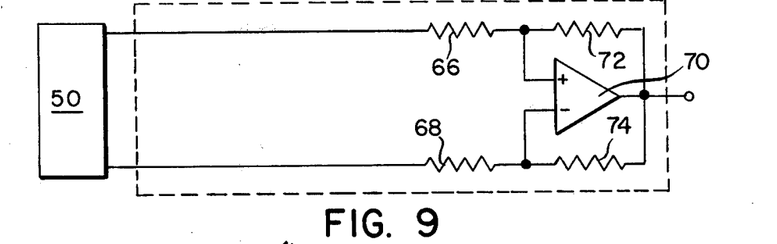
FIG. 9 is a schematic diagram of a processor which is especially adapted to calculate the ratio of concentration at selected stations.

An especially useful configuration for the processor 62 is shown in FIG. 9 in which the outputs of two of the photodetectors of the densitometer 50 are applied through resistors 66, 68 to the respective input terminals of a high-gain amplifier 70 having feedback resistors 72, 74 connected around it. The photocells provide outputs proportional to the logarithm of the density of the particle concentration as measured at corresponding stations of the densitometer 50. The amplifier 70, with its associated resistors, provides an output proportional to the difference between these two logarithms. Since the difference between the logarithms of two quantities is identical to the logarithm of the ratio of these quantities, the output of the amplifier 70 is proportional to the logarithm of the ratio of the quantity of the particulate deposited at one station with respect to the quantity of particulate deposited at the other. This quantity is thus monitored as one indication of the operating condition of an engine whose engine oil is being examined. For example, if, after remaining substantially constant for a period of time, the ratio should increase in a manner corresponding to a sudden increase in the number of larger particles relative to smaller particles at the stations being monitored, a direct indication of a possible malfunction is obtained on noting the increase and corrective action may be taken.

In addition to observations of particle size, particle size distribution, and trends (changes with time in these parameters), the present invention is useful in providing indications of the nature of the various particles observed. This is a consequence of the fact that the sparsely distributed particles are removed from the oil in which they are suspended and concentrated on a substrate so that individual particles, or groups of particles, may readily be examined. Heretofore, because of the small size and concentration of the particles suspended in the oil or other fluid being analyzed, they could not practicably be examined microscopically. Further, even where the particles of interest were sufficiently large to be so examined, they were often obscured by the presence of other (generally non-magnetic) particles not of interest, such as carbon particles, etc. Those particles which were sufficiently large to be separated from the solution by mechanical or chemical means might be examined in the dry state by incident light since, by virtue of their large size, they were generally opaque. However, even here, limitations appear. Thus, in mechanically filtering particles, the particles tend to pile on top of one another and this obscures observation of individual particles. Further, examination by incident light alone obscures some of the information which I have found can be obtained.

Accordingly, In have developed techniques for optically examining particulate deposites on substrates to determine characterostics of the particles in addition to size distribution and density. Briefly, I illuminate the concentrated particles with both incident (reflected) and transmitted light of different colors. For example, a soucre of green light may be utilized for the transmitted light and a source of red light for the incident light. The use of different colors allows one to readily distinguish the respective contributions of the incident and the transmitted light to the resultant image and thus to distinguish such materials as oxides and sulfides (which are translucent when the particles are of the dimensions considered here, i.e. on the order of a micron) from materials such as metals (which are opaque, even when as small as one micron). With this lighting arrangement, the oxides and sulfides appear as discernible green or yellow while the metals are readily distinguishable as being pink in color. In cases in which the various components can be correlated with different portions of an engine, the present invention therefore allows one to determine not only the wear characteristics of an engine, but also to determine the relative contributions to the wear from the different portions of the engine. This may be especially helpful in diagnosing a faulty engine part and enabling one to go directly to the part which may be failing, without having to disassemble each portion of the engine to determine the failure point.

Figure 10:
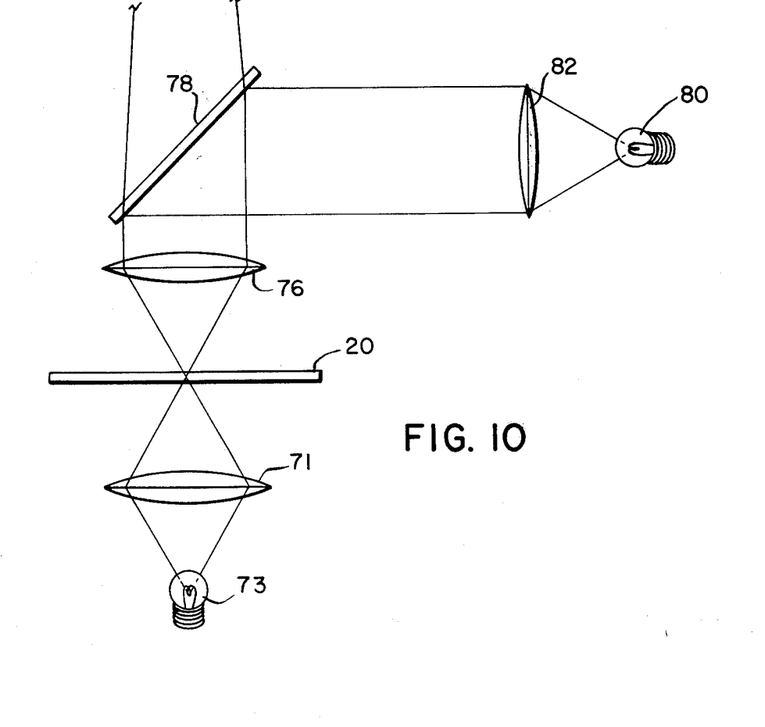
FIG. 10 is a sketch of a portion of a transmitting-reflecting microscope suitable for examining the slide of FIG. 2.

A microscope setup which is especially advantageous for examining the substrate for the foregoing purposes is illustrated in FIG. 10. As shown therein, a light source 73 supplies light through a substage condenser lens 71 to the substrate 20. This light is transmitted through the substrate into an objective lens 76 and thence into the eyepiece (not shown) of a microscope through a half silvered mirror 78. Similarly, a light source 80 supplies light to the substrate 20 through a second condensing lens 82, half-silvered mirror 78, and objective lens 76. This light is reflected from the substrate 20 and returned to the eyepiece of the microscope through the lens 76 and the half silvered mirror 78. The source 73 which is the source of transmitted light, is characterized by a first color, e.g. green, while the source 80, whicb is the source of reflected light, is characterized by a second color, e.g., red. This may be achieved by inserting appropriate filters (not shown) into the respective light paths.

Figure 11:
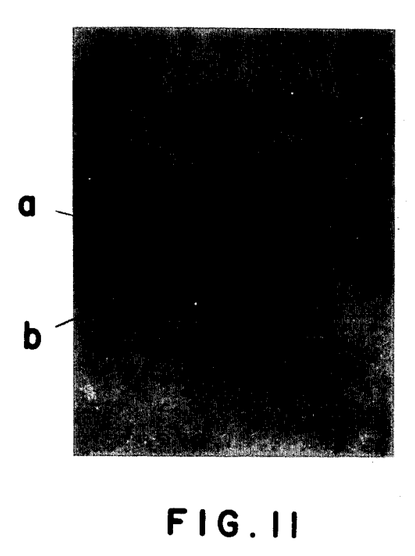
FIG. 11 is a reproduction of a photomicrograph obtained with the microscope of FIG. 8.

This technique effectively optically "stains" the material being examined to expose its fine structure. A vivid illustration of the usefulness of this technique is shown in FIG. 11 which is a photomicrograph of the precipitate from an oil sample taken at a magnification of 645 times. In this particular example, the incident light was red in color while the transmitted light was green. The large particle (designated by an arrow) in the center is an iron particle and is readily seen to comprise a large oxide ("rust") segment $a$ and an as yet "unrusted" metallic segment $b$ of smaller size. Knowledge of the presence of particles from an oxidizing portion of the engine enables further identification of engine malfunction. Although the contrast is not as distinct in this black-and-white reproduction, it shows up distinctly in a color photograph. Thus, by optically "standing" the substrate being examined, characteristics otherwise hidden become apparent.

So far I have described the operation of the invention in connection with external type monitoring apparatus. Although this will be adequate in many cases, it will often be found desirable to monitor the operation of an engine or other piece of machinery during normal operation. For example, it would be extremely beneficial to monitor the engine oil in the jet engines of an aircraft during actual flight in order to obtain early indications of possible malfunctions so that preventive action may be taken.

Figure 12:
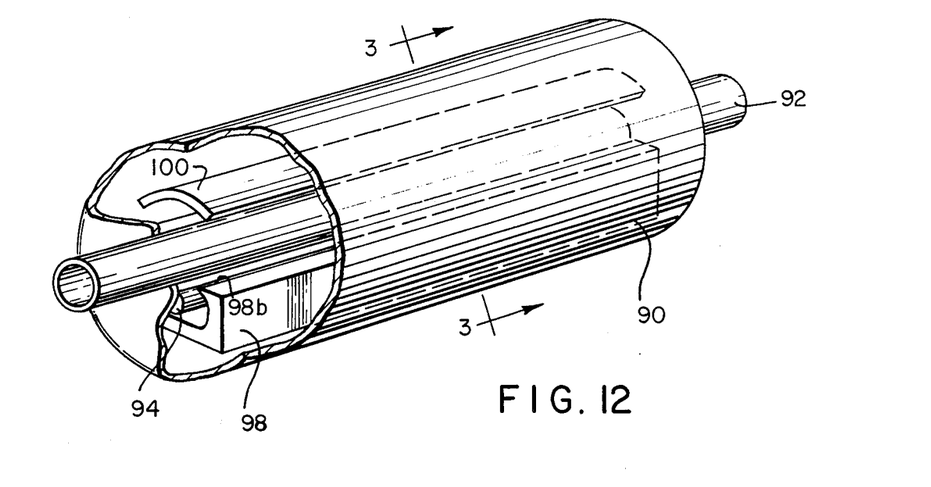
FIG. 12 is a pictorial view of another form of apparatus in accordance with the present invention, especially adapted for in situ measurements.
Figure 13:
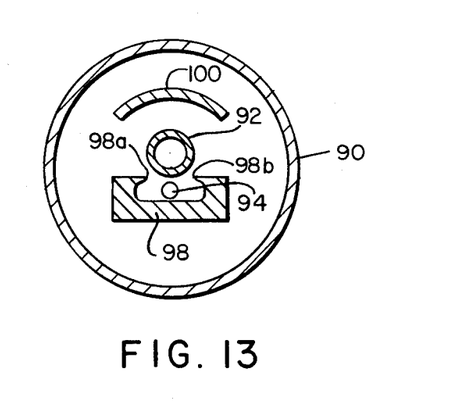
FIG. 13 is a vertical cross section along the lines 11—11 of FIG. 10.

One embodiment of the invention which is especially suited to this application is illustrated in FIGS. 12 and 13 in which a shell or housing 90, adapted for mounting in an engine, has a translucent cylindrical tube 92 extending longitudinally through it and connected as a minor bypass in the oil line. The tube 92 receives light from a light source 94 positioned beneath it; a reflector (not shown) may be positioned beneath the light source for concentrating the light from source 94 onto the tube 92. A magnet 98 is high field strength and having sharp "leading edges" 98$a$, 98$b$, is positioned adjacent the tube 92 and projects a field through the tube. A densitometer 100 is located above the tube 92 opposite light source 94. As was the case with the densitometer 50 of FIG, 8, the densitometer 100 has one or more light transmitting aperatures (not shown) behind which photocells (also not shown) are positioned for receiving light from corresponding stations on the tube 92. The output of the densitometer is applied to processing and display apparatus (not shown).

In operation, as the engine oil flows through the tube 92, it is subjected to the action of the magnet 98 which causes suspended magnetic particles to precipitate onto the interior wall of the tube. The tube is positioned above the gap between the pole edges 98a, 98b with its longitudinal axis inclined slightly away from the plane of the leading edges 98a, 98b from one end of the tube toward the other so as to provide a gradually increasing magnetic field, as was the case in FIG. 1. This assists in precipitating particles on the inside wall of the tube 92 in accordance with their size. The particle concentration is monitored by means of the densitometer 100.

The magnet 98 is preferably an electromagnet which can be turned on and off by the user. Then, after the particles have been collected for a certain period of time and their concentrations measured, the electromagnet is switched off. This allows the oil to flush the particles from the tube in preparation for a new measurement. This may be coupled with a flush bypass switch (not shown) which ports oil to the tube 92 only when measurements are to be made.

Various parameters of the particles, as measured by the densitometer, may be selected for processing and display. For example, the particle concentrations at the various stations as determined from the optical densities measured at the stations by the densitometer, the rate at which these concentrations change, the ratios of concentrations, etc. may all be determined and displayed to provide an indication of engine performance. The measurement and/or display may, of course, be continuous or intermittent, as desired.

Figure 14:
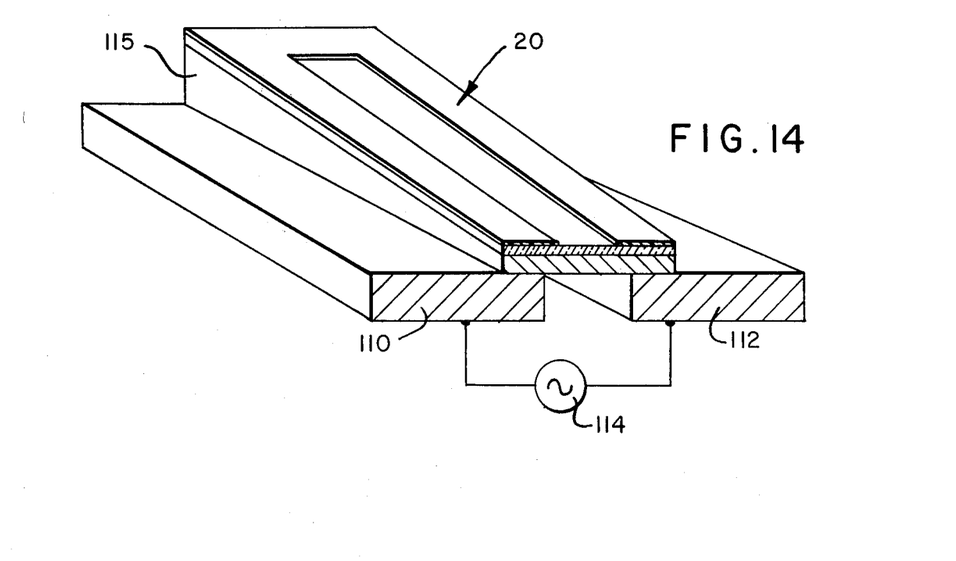
FIG. 14 is a view in perspective of an electrostatic form of apparatus in accordance with the invention.

The electrical analog of the technique so far described may also advantageously be utilized, especially where the particles to be collected are non-magnetic. A sketch of an electrical collector of this type is shown in FIG. 14 in which the conventional substrate 20 is positioned above flat, planar electrodes 110, 112 between which a highly divergent electric field of high intensity is established by a voltage source 114 which may advantageously be a 60 cycle source. A wedge 115 (shown greatly enlarged for purpose of illustration only), maintains the substrate is sloping relation to the electrodes 110, 112 to establish an increasingly intense field as fluid flows along the substrate from rear to front in FIG. 14. Prefereably, the wedge provides a slope of about 1° for this purpose.

The operation of this device is similar to that of the magnetic device of FIG. 1, i.e. the electrodes 110, 112 project a high intensity, non-uniform (i.e. highly diverging) field into the gap between them so thatj polarizable particles are precipitated from solution by this field in the same manner that magnetically susceptible particles are precipitated by the magnetic field. For particles of the size under consideration here (i.e. micron sized particles) a gap of 0.020 inch in conjunction with a potential difference of 1000 volts to create a field of 50,000 volts/inch is desirable.

Although I have described my invention with particular reference to observing wear characteristics of machinery, it should be understood that it has broad applicability to other uses. Thus, as noted earlier, it also provides an especially convenient and rapid means of testing the performance of lubricants. Further, it may be used to monitor "contaminents" which have purposefully been introduced into a fluid to check for leakage in a system, track flow paths, etc. Other applications will readily suggest themselves to the user. Further, while I anticipate that my invention will be used primarily to monitor the sizes and size distributions of uncharged magnetically or electrically susceptible particles for which a divergent magentic or electric field is required to create the appropriate precipitating forces, it will be understood that in some instances uniform force fields or force fields other than magnetic or electric may be adapted to create the desired distribution.

From the foregoing it will be seen that I have provided a useful and sensitive method for measuring the relative concentration of particles of different sizes. The method may be applied to either magnetically susceptible particles or to electrically polarizable particles, but is especially useful for measuring the relative concentrations of particles of iron in a fluid a such as engine oil. In this connection it is important to note that my system detects free iron and iron-containing magnetically susceptible or electrically polarizable particles as opposed to chemically combined iron forms which may be not necessarily result from engine wear. Further, the method can be utilized for making measurements external to the engine or machinery whose performance is being monitored, or can be readily instrumented to make the desired measurements in situ.

Further, I have described a kit which is especially useful in practicing the invention. Containing at least one substrate, a "developer"]serving as a precipitation-promoting agent, a "fixer" serving as a cleanser, and a supply of flexible tubing for carrying the developer and fixer to the substrate, (a "fixer" for cleansing the "developer" from the substrate will generally be found desirable but may in some cases be omitted) it provides all the components (except for a pump, a means for generating an appropriate force field, and a substrate analyzer) required for monitoring particle concentration in a fluid under conditions which ensure that the fluid sample will not be contaminated by previous samples which have been processed. Subsequent samples are preserved from contamination, of course, by disposing of the used tubing, developer, and fixer after each fluid sample is processed.

In addition, I have set forth a useful technique for analyzing tthe precipitate partterns obtained in accordance with the method of the invention. This technique allows the acquisition of information concerning the composition of the precipitate material, in addition to the information concerning particle size distribution and precipitation rates otherwise obtained from the samples.

It will be understood by those skilled in the art that various changes can be made in the foregoing method and apparatus without departing from either the scope or the spirit of the invention. Further, while the invention has been described with particular reference to the measurement of iron concentration, in engine oil, it will be understood that it is not so limited and that it may be used to monitor and measure the concentration, rate of change of concentration, concentration ratios, etc. of any magnetically susceptible or electrically polarizable particle in a fluid medium.

Having described the invention, I claim:

1. A method of classifying hyperfine particles in a fluid medium according to their size, comprising the steps of:

A. positioning a substrate within a force field having a component of relatively high intensity extending orthogonal to a flow-supporting surface of said substrate and attracting toward said surface particles adjacent said surface;

B. flowing a particle-containing fluid medium along an extended path on said substrate surface of interaction with said field whereby the field precipitates particles onto said substrate according to their size, the larger particles first.

2. A method according to claim 1 in which the flow rate and field intensity are such that larger particles are collected over a portion of said path that is substantially less than its length.

3. A method according to claim 2 in which said particles are magnetically susceptible and in which said field is a magnetic field of high divergence adjacent the path.

4. A method according to claim 2 in which said particles are electrically polarizable and in which said field is an electric field of high divergence adjacent the substrate surface.

5. A method according to claim 2 in which said particles are electrically charged and said field is an electric field.

6. The method of claim 1 in which said substrate is so positioned in said field that the force created by said field increases from a first portion of said substrate to a second portion thereof in the direction of fluid flow over the substrate whereby particles to be collected are subjected to increasing forces as the substrate is traversed.

7. The method of claim 1 which includes the step of monitoring the density of particles precipitated onto said substrate by said field at at least two distinct stations spatially spearatseparated from each other in the direction of fluid flow.

8. The method of claim 7 which includes the step of monitoring the ratio of the precipitate concentrations at pairs of said stations.

9. The method of claim 7 which includes the step of monitoring the ratio of the time rate of change of precipitate concentration at pairs of said stations.

10. The method of claim 1 in which said substrate is light-transmitting and which includes the step of monitoring the particle characteristics by means of a microscope which illuminates the precipitate with reflected light of a first color and transmitted light of a second color, whereby particles may be distinguished by means of their light transmission and light reflection characteristics.

11. The method of claim 1 in which the substrate is light-transmitting and which includes the step of monitoring the particle characteristics by means of a photosensitive medium and a light source positioned to transmit light through said substrate into said medium, said precipitate diminishing the light transmission in accordance with the concentration of the precipitate on the substrate.

12. The method of claim 1 in which the substrate is a relatively thin planar slide oriented to support the movement of said fluid along a surface thereof.

13. The method of claim 12 in which said force field is generated by a magnetic field having a gradient component of the order of hundreds of kilogauss per inch orthogonal to said slide for attracting magnetically susceptible particles thereto.

14. The method of claim 1 which includes the step of accelerating the particle precipitation rate by mixing a chemical additive with said fluid prior to flowing said fluid over said substrate.

15. The method of claim 14 in which said additive includes a developer comprising perchlorethylene.

16. The method of claim 15 which includes the step of removing said developer by washing the substrate surface with a fixer comprising trichlorethylene after said fluid is flowed over said substrate.

17. A method of examining micron-sized particles deposited on a translucent substrate, comprising the steps of:
  A. illuminating the substrate from a radiation source characterized by a first wavelength and positioned to transmit said radiation along a first path through said substrate and into an imaging element;
  B. illuminating the substrate from a radiation source characterized by a second wavelength different from said first wavelength and positioned to transmit said radiation along a second path impinging on said substrate from a direction oposite to said first path for reflection into said imaging element;
  C. examining the image formed by the simultaneous reception of radiation from both said sources.

18. A method according to claim 17 in which said radiation is at optical frequencies with said first and second wavelengths corresponding to light of different colors and in which said examination is by means of an imaging eyepiece.

19. In connection with the separation of particles from a fluid medium and their segregation in accordance with particle size, the improvement comprising particle concentration, classification and recording apparatus for use with a magnet supplying an intense inhomogeneous field, said apparatus comprising:
  A. a substrate;
    1. for positioning in said field;
    2. for supporting fluid flow of said particle-containing fluid over a surface thereof and receiving particles from said fluid thereon;
    3. providing a record of particles collected thereon and segregated according to particle size;
  B. a container holding precipitation-accelerating agent for mixing with said fluid to promote the separation of particles therefrom by said field when said fluid is flowed over said substrate; and
  C. tubing for transporting said fluid and said agent to said substrate.

20. Apparatus according to claim 19 in which the means for carrying the fluid and the accelerating agent to the substrate comprises flexible tubing adapted for use in conjunction with a positive displacement pump which advances fluids in the tubing without contact therewith.

21. Apparatus according to claim 19 in which the accelerating agent comprises perchlorethylene.

22. Apparatus according to claim 19 which includes an agent for removing the accelerating agent from the substrate and from the particles deposited thereon.

23. Apparatus according to claim 22 in which the removing agent comprises trichlorethylene.

24. Apparatus according to claim 19 in which said substrate comprises a thin (of the order of mils) generally rectangular slide.

25. Apparatus according to claim 24 in which said substrate includes a flow confining means on a fluid receiving surface thereof whereby said flow may be confined to a selected portion of the substrate.

26. Apparatus for monitoring selected characteristics of particles predominately of micron size or less and contained in a fluid medium, said apparatus comprising:

A. means for supporting a substrate having a surface of sufficient length to receive the fluid medium for flow along an extended path thereon;

B. means for applying said fluid to said substrate surface at a controlled rate for flow along said path; and C. means for establishing a force field having a force component directed toward the fluid-receiving surface for precipitating fluid-suspended particles onto said surface as they flow along said paths, the larger particles being precipitated first.

27. Apparatus according to claim 26 in which the particles to be monitored are magnetically polarizable and the means for establishing a force field comprises a magnet which generates a diverging magnetic field at the fluid-receiving surface of said substrate when the substrate is positioned on the supporting means whereby magnetically susceptible particles are drawn onto the substrate by the magnetic field.

28. Apparatus according to claim 27 in which the magnet is so oriented to the fluid-receiving surface of the substrate when the substrate is positioned on the supporting means that the force field generated at said surface by said magnet increases in the direction of fluid flow along said substrate surface whereby particles in said fluid are subjected to increasing forces as said substrate is traversed.

29. Apparatus according to claim 27 in which the magnet establishes a gradient of the order of hundreds of kilogauss per inch in a direction generally orthogonal to the substrate surface.

30. Apparatus according to claim 29 in which said magnet has opposed, wedge-shaped pole faces terminating in coplanar apexes between which said field is generated and in which the substrate surface onto which the particles are collected has a lateral dimension extending across said gap generally parallel to a plane connecting the apexes of said wedges and a longitudinal dimension transverse to said lateral dimension and inclined at an angle to the plane connecting said apexes.

31. Apparatus according to claim 26 in which the particles to be monitored are electrically polarizable and the means for establishing a force field comprises a source of alternating electrical potential which generates a diverging electric field at the fluid-receiving surface of the substrate when the substrate is positioned on the supporting means whereby electrically polarizable particles are drawn onto said substrate by the electric field.

32. Apparatus according to claim 31 in which the source of electrical potential establishes a gradient of the order of kilovolts per inch in a direction generally orthogonal to the substrate surface.

33. Apparatus according to claim 26 in which the means for applying the fluid to the substrate surface includes:

A. a run of flexible tubing extendable between a source of said fluid and the substrate; and B. means for progressively forcing fluid along the interior of said tubing by squeezing said tubing.

34. Apparatus according to claim 26 which includes means for monitoring the density of the particles precipitated onto the substrate at selected locations on said substrate.

35. Apparatus according to claim 34 in which the monitoring apparatus comprises an optical densitometer.

36. Apparatus according to claim 26 in which said substrate comprises a tube for carrying the particle-containing fluid and adapted to transmit illumination directly through at least a portion thereof, and which further includes:

A. an illuminating source positioned adjacent said tube for projecting illumination therethrough; and B. illumination responsive means positioned to receive illumination transmitted through said tube for examination of particles attracted to said surface by said field.

37. Apparatus according to claim 36 including a generally closed shell enclosing the tube, the illuminating source and the illumination responsive means on the interior thereof and having first and second apertures coincident with first and second tube openings on opposed ends of said tube whereby fluid may be flowed through the tube within the shell for analysis.

38. Apparatus according to claim 37 in which said tube is oriented with respect to the field gradient in such a manner that, as the field gradient increases from one end of the tube to the other, differing forces are presented to particles in the fluid medium at different positions along the tube to thereby facilitate the precipitation of particles along the tube in accordance with their size.

39. Apparatus according to claim 37 in which the illumination responsive means is adapted to provide a plurality of outputs corresponding to reception of illumination transmitted through said tube at a corresponding plurality of different segments along said tube whereby the concentrations of the precipitate at said segments may be monitored.

40. Apparatus according to claim 39 which includes means for calculating the ratios of said concentrations.

41. Apparatus according to claim 40 which includes means for calculating the time rate of change of said ratios.

42. Apparatus according to claim 40 which includes means for periodically purging collected particles from the tube to facilitate repeated measurements of the precipitate concentration therein.

43. A method of classifying particulate matter in a fluid medium by segregating the particles according to the relative motion-responsiveness thereof to a force field while the particles are in a fluid medium, comprising the steps of:

A. positioning a substrate within a force field having a force-producing component of relatively high intensity extending orthogonal to a flow-supporting surface of said substrate and attracting toward said surface particles adjacent said surface;

B. flowing a particle-containing fluid medium along an extended path on said substrate surface for interaction with said field with individual particles responding to said field with differing rates of movement towards said substrate in accordance with their force-field responsiveness, said field precipitating the particles onto said substrate according to their relative force-field-responsiveness with the more responsive particles precipitating first.

44. Apparatus for monitoring force-field-responsive particles contained in a fluid medium, said apparatus comprising:

A. means for supporting a substrate having a surface of sufficient length to receive the fluid medium for flowing along an extended path thereon;

B. means for applying said fluid to said substrate surface at a controlled rate for flow along said path; and C. means for establishing a force field having a force component directed toward the fluid-receiving surface for precipitating fluid-suspended particles onto said surface as they flow along said path, the particles which are more highly field-responsive being precipitated first.

45. A method of separating hyperfine particles in a fluid medium by segregating the particles as a function of their differing relative rates of motion in accordance with their force-field responsiveness while they are within the fluid medium, comprising the steps of:

A. positioning a substrate within a force field having a component of relatively high intensity extending orthogonal to a flow-supporting surface of said substrate and attracting toward said surface particles adjacent said surface;

B. flowing a particle-containing fluid medium along an extended path on said substrate surface having a predetermined beginning and end for allowing the particles within said fluid medium to interact with said field for causing individual particles in said fluid medium to respond to said field with differing rates of movement towards said substrate in accordance with their force-field responsiveness;

C. providing a spacing between the beginning and end of said path which is sufficiently long relative to the flowing rate of said fluid medium that a significant amount of said particles will precipitate onto said substrate according to their relative force-field-responsiveness with the more responsive particles precipitating nearer the beginning of said path while the particles of lesser responsiveness precipitate nearer the end of said path, thereby providing a spacial distribution along said substrate of the particles precipitated from said fluid medium.

46. Apparatus for monitoring the relative rates of motion in response to an applied force field of force-field-responsive particles predominately of micron size or less and contained in a fluid medium, said apparatus comprising:

A. means for supporting a substrate having a surface of sufficient length to receive the fluid medium for flow along an extended path thereon from a beginning point to an ending point;

B. means for applying said fluid to said substrate surface at a controlled rate for flow along said path from said beginning point to said ending point; and C. means for establishing a force field having a force component directed toward the fluid-receiving surface for precipitating fluid-suspended particles onto said surface as they flow along said path, the particles which are more highly field-responsive being precipitated nearer to the beginning point of said path.

47. A method of segregating particles in accordance with the responsiveness of the particles to a force field, comprising the steps of:

A. positioning a particle-displaying substrate within a force field having a component of relatively high intensity extending orthogonal to a flow-supporting surface of said substrate;

B. placing said fluid in a container with a precipitating-accelerating agent to form a mixture therewith;

C. drawing said fluid-and-agent mixture from said container through a tube inserted at one end in said container;

D. directing the flow of said mixture from the other end of said tube onto said substrate;

E. flowing said mixture along an extended path on said substrate surface for interaction with said force field, with particles in said mixture being moved by the force of said field so as to precipitate onto said substrate according to their force-field-responsiveness, the more responsive particles precipitating first.

* * * * *